United States Patent
Comaniciu et al.

(10) Patent No.: US 10,282,588 B2
(45) Date of Patent: May 7, 2019

(54) IMAGE-BASED TUMOR PHENOTYPING WITH MACHINE LEARNING FROM SYNTHETIC DATA

(71) Applicant: Siemens Healthcare GmbH, Erlangen (DE)

(72) Inventors: Dorin Comaniciu, Princeton Junction, NJ (US); Ali Kamen, Skillman, NJ (US); David Liu, Richardson, TX (US); Boris Mailhe, Plainsboro, NJ (US); Tommaso Mansi, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/584,393

(22) Filed: May 2, 2017

(65) Prior Publication Data

US 2017/0357844 A1    Dec. 14, 2017

Related U.S. Application Data

(60) Provisional application No. 62/347,864, filed on Jun. 9, 2016.

(51) Int. Cl.
*G06K 9/00* (2006.01)
*G16B 40/00* (2019.01)
(Continued)

(52) U.S. Cl.
CPC ......... *G06K 9/00127* (2013.01); *G06F 19/30* (2013.01); *G06K 9/00536* (2013.01);
(Continued)

(58) Field of Classification Search
CPC ............... G06K 9/00127; G01N 2800/7028
See application file for complete search history.

(56) References Cited

U.S. PATENT DOCUMENTS

| | | | |
|---|---|---|---|
| 2013/0129196 A1* | 5/2013 | Paris .................. | G06K 9/62 |
| | | | 382/155 |
| 2013/0202173 A1* | 8/2013 | Buckler ............... | G06T 7/0012 |
| | | | 382/131 |

(Continued)

OTHER PUBLICATIONS

Zimmerman, J. R., and W. E_ Brittin. "Nuclear magnetic resonance studies in multiple phase systems: lifetime of a water molecule in an adsorbing phase on silica gel." The Journal of Physical Chemistry 61.10 (1957): 1328-1333.

(Continued)

*Primary Examiner* — Oneal R Mistry

(57) ABSTRACT

Machine training and application of machine-trained classifier are used for image-based tumor phenotyping in a medical system. To create a training database with known phenotype information, synthetic medical images are created. A computational tumor model creates various examples of tumors in tissue. Using the computational tumor model allows one to create examples not available from actual patients, increasing the number and variance of examples used for machine-learning to predict tumor phenotype. A model of an imaging system generates synthetic images from the examples. The machine-trained classifier is applied to images from actual patients to predict tumor phenotype for that patient based on the knowledge learned from the synthetic images.

20 Claims, 2 Drawing Sheets

(51) Int. Cl.
  *G16B 45/00* (2019.01)
  *G06F 19/00* (2018.01)
  *G16H 30/00* (2018.01)
(52) U.S. Cl.
  CPC ......... *G06K 9/00885* (2013.01); *G16B 40/00* (2019.02); *G16B 45/00* (2019.02); *G16H 30/00* (2018.01); *G01N 2800/7028* (2013.01)

(56) References Cited

U.S. PATENT DOCUMENTS

| | | | |
|---|---|---|---|
| 2015/0087957 A1* | 3/2015 | Liu | G06T 7/42 600/408 |
| 2015/0213302 A1* | 7/2015 | Madabhushi | G06K 9/00147 382/133 |
| 2016/0148371 A1 | 5/2016 | Itu et al. | |
| 2017/0053398 A1* | 2/2017 | Mahoor | G06T 7/0012 |
| 2017/0091937 A1* | 3/2017 | Barnes | G06T 7/0012 |

OTHER PUBLICATIONS

Cecchin, E., et al. "Tumor response is predicted by patient genetic profile in rectal cancer patients treated with neo-adjuvant chemo-radiotherapy." The pharmacogenomics journal 11.3 (Jun. 2011): 214-226.

Itu, Lucian, et al. "A machine-learning approach for computation of fractional flow reserve from coronary computed tomography." Journal of Applied Physiology 121.1 (2016): 42-52.

Konukoglu, Ender, et al. "Image guided personalization of reaction-diffusion type tumor growth models using modified anisotropic eikonal equations." IEEE transactions on medical imaging 29.1 (2010): 77-95.

Perthame, Benoît. "Some mathematical aspects of tumor growth and therapy." ICM 2014—International Congress of Mathematicians. 2014.

Rapaka, Saikiran, et al. "LBM-EP: Lattice-Boltzmann method for fast cardiac electrophysiology simulation from 3D images." Medical Image Computing and Computer-Assisted Intervention—MICCAI 2012 (2012): 33-40.

Ribba, B., et al. "A review of mixed-effects models of tumor growth and effects of anticancer drug treatment used in population analysis." CPT: pharmacometrics & systems pharmacology 3.5 (2014): 1-10.

Wong, Ken CL, et al. "Tumor growth prediction with reaction-diffusion and hyperelastic biomechanical model by physiological data fusion." Medical image analysis 25.1 (2015): 72-85.

Strijkers, Gustav J., et al. "Three-compartment T1 relaxation model for intracellular paramagnetic contrast agents." Magnetic resonance in medicine 61.5 (2009): 1049-1058.

Tang, Lei, et al. "Computational modeling of 3D tumor growth and angiogenesis for chemotherapy evaluation." PloS one 9.1 (2014): e83962.

Tofts, Paul S., et al. "Estimating kinetic parameters from dynamic contrast-enhanced T 1-weighted MRI of a diffusable tracer: standardized quantities and symbols." Journal of Magnetic Resonance Imaging 10.3 (1999): 223-232.

Wang, Zhihui, et al. "Simulating cancer growth with multiscale agent-based modeling." Seminars in cancer biology. vol. 30. Academic Press, 2015.

* cited by examiner

IMAGE-BASED TUMOR PHENOTYPING WITH MACHINE LEARNING FROM SYNTHETIC DATA

RELATED APPLICATIONS

The present patent document claims the benefit of the filing date under 35 U.S.C. § 119(e) of Provisional U.S. Patent Application Ser. No. 62/347,864, filed Jun. 9, 2016, which is hereby incorporated by reference.

BACKGROUND

The present embodiments relate to medical diagnosis, treatment planning, and/or prognosis for tumors.

Imaging is an important diagnostic tool for the prediction and monitoring of the treatment response of cancer. Current approaches generally rely on aggregate characteristics of the tumor derived from medical images. The characteristics may include tumor size (e.g., measured as linear dimensions or volume) or intensity parameters (e.g. perfusion properties). These approaches do not account for the rich information available from the spatial distribution of tumor substrate and physiology, often captured by the texture and multi-parametric spatial patterns of anatomical, physiological, and molecular images. This is the case for response prediction from single image time point or from changes in images as a function of time.

SUMMARY

By way of introduction, the preferred embodiments described below include methods, computer readable media and systems for machine training and application of machine-trained classifier for image-based tumor phenotyping in a medical system. To create a rich-enough training database with known phenotype information, synthetic medical images are created. This is crucial as each tumor is unique and data augmentation is necessary for optimal performance of machine-trained algorithms. A computational tumor model creates various examples of tumors types. Using the computational tumor model provides training data examples not available from actual patients, increasing the number and variance of examples used for machine-learning to predict tumor phenotype. A model of an imaging system generates synthetic images from the examples. The machine-trained classifier is applied to images from actual patients to predict tumor phenotype for that patient based on the knowledge learned from the synthetic images.

In a first aspect, a method is provided for image-based tumor phenotyping in a medical system. Medical scan data representing a tumor in tissue of a patient is acquired. A set of features are extracted from the medical scan data. The features are input to a machine-trained classifier. The machine trained classifier is trained, at least in part, from synthetically generated images not specific to training data for existing patient cases and based on a tumor model. By application of the machine-trained classifier to the features, phenotype information of the tumor is determined. The phenotype information is output.

In a second aspect, a method is provided for machine training for image-based tumor phenotyping in a medical system. Parameters of a computational tumor model are varied. The varying provides a set of synthetically generated examples of tumors. Medical images are emulated from the synthetically generated examples of tumors. A machine trains a machine-learnt classifier using the emulated medical images.

In a third aspect, a method is provided for machine training for image-based tumor phenotyping in a medical system. Tumor growth or shrinkage is modeled. Synthetic images are created with an image model from the modeling of tumor growth or shrinkage. A machine is trained to predict from a database of training data including the images created from the modeling of the tumor growth or shrinkage.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
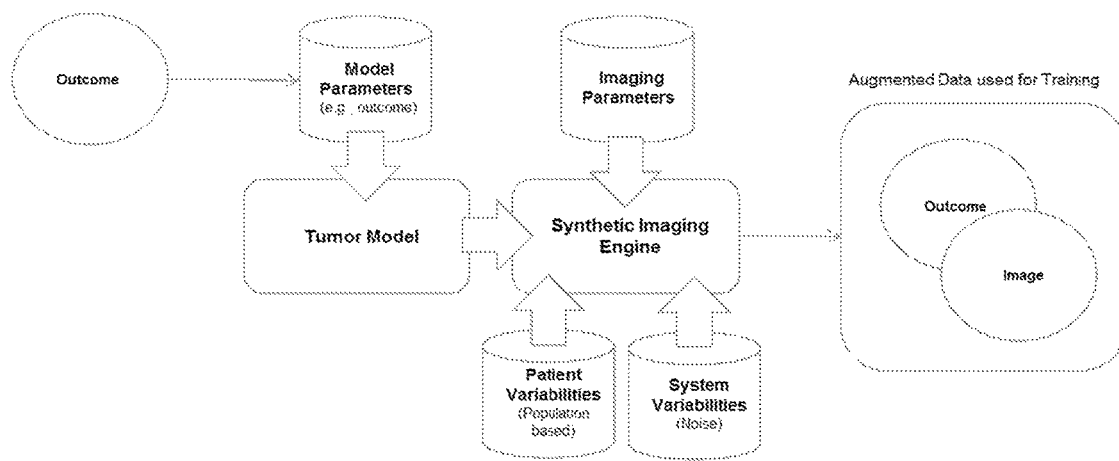
FIG. 1 is an arrangement showing machine learning based on computational models of tumors.

The collection of data from patient images and measurements presents a very complex network of information about the patient. This complex network of information may be effectively untangled by modern machine learning algorithms. A machine-learnt classifier provides fast patient assessment and outcome analysis. Modern machine learning and artificial intelligence algorithms are well suited to managing large quantities of heterogeneous data. Consistent predictions are provided in an automated manner. Machine learning algorithms have superior predictive capabilities in complex tasks, showing expert-level performance. A comprehensive patient assessment model combines all available information from the patient to present an integrated understanding of the patient state as well as enable the clinician to guide therapy.

Machine learning may be used for image-based non-invasive tumor phenotyping for diagnosis, prognosis and therapy. Quantifying tumor phenotypic characteristics that predict and reflect progression in response to specific treatments and relate to ultimate patient outcome may potentially benefit significantly from automated computer analysis for several reasons. Computer analysis is highly reproducible and does not depend on subjective evaluation. Precise quantification is likely to improve detection of subtle characteristics of the tumor and change in response to treatment, which predicts future outcome. Machine learning tools trained using large amounts of data may be very effective in identifying which imaging (and non-imaging) features and patterns, as well as their change with treatment, are best predictors of diagnosis, response, and/or outcome and serve as knowledge discovery tools.

For personalized tumor treatments, cancer is being categorized at an increasingly finer scale. Image features, clinical data, patient history, and/or genetic testing, for example, are used to uniquely identify a tumor phenotype. In such situations, every cancer becomes a unique disease. To train a machine-learnt classifier for each phenotype requires access to many examples for each phenotype. Due to the fine scale, such data from actual patients may not be available in sufficient quantities and/or may be difficult to acquire. As a result, it becomes extremely challenging to acquire the necessary amount of data to train complex radiomics or radiogenomics machine-learnt systems without data augmentation.

Synthetic examples may be used to augment the training database. The feature detection and learning paradigm is based on synthetic samples created using multi-scale models of tumor phenotypes rather than starting with synthetic examples of images. The aim is to not only detect subtle phenotypical patterns but also relate them to known root causes closer to the molecular or cellular level given models based on lower scale physiological and/or molecular information. To cope with the limited amount of available labelled data for training, multi-scale models of tumor growth are coupled with imaging models to create synthetic images for machine learning.

FIG. 1 shows one embodiment of a method for training a machine learnt classifier to output tumor phenotype information. The training data is augmented. The training data includes examples of images of tumors and the labeled ground truth or outcome (e.g., phenotype information). The tumor model receives various sets of values of parameters to generate example tumors. Sample data points use models of tumor to reflect apparent change in the images for differences in the tumor. The synthetic imaging engine receives image parameters, the example tumors, system variabilities (e.g., modeled noise from imaging), and/or other patient data that effect the simulation of imaging. The synthetic imaging engine creates example images with the outcomes as a database of model-driven training data. A knowledge driven set of data is created where not only the already discovered knowledge is represented but also the variabilities from patient population, image formation, and overall system noise is incorporated. Other methods with different, additional, or fewer acts may be provided.

In one embodiment, an augmented, synthetic database of images with virtual tumors having known cellular and tissue properties is created. Each image of the database is generated by acquiring an image template, selecting an organ, performing virtual tumor modeling within the selected organ, and generating a virtual cancer, creating a synthetic image with the virtual cancer, and adding the synthetic image to the database. The machine trains a radiomics or radiogenomics predictive model from the augmented, synthetic database, which can be complemented with real patient data. The radiomics or radiogenomics model is a model for early tumor diagnosis, active surveillance using early-stage tumor models, and/or a model for virtual biopsy. The radiomics or radiogenomics model is applied to unseen image data for diagnosis, monitoring, and/or therapy planning for a patient.

In one approach, the synthetic samples are created using models of tumor physiology, including growth, infiltration, metastasis, and/or shrinkage due to a therapy, based on lower scale physiological information (e.g., either based on the patient data or a set of population-based parameters). For example, at a high level, through established studies, it has been discovered that patients with certain demographics and genetic dispositions have a certain pattern of tumor growth with specific levels of angiogenesis, hypoxia, tumor shape irregularity. This "model" may be a basis for generating synthetic samples of this phenotype for training, where variability is introduced to these and/or other aspects of the tumor characteristics such as density, location, and size. This "model based" generated training set of outcome matched images may allow the learning process to focus on what is known and incorporate dictated variabilities. Fully data driven learning through synthetic labeled data augmentation is based on what has already been discovered embodied by various tumor models.

Figure 2:
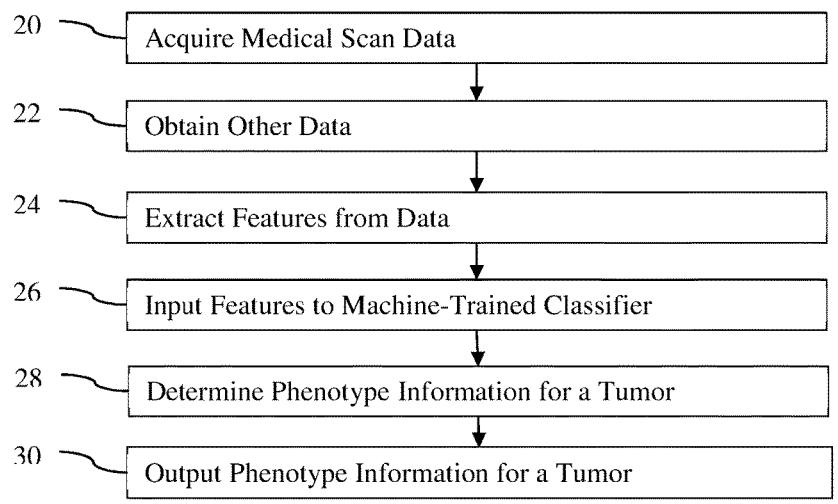
FIG. 2 is a flow chart of one embodiment of a method for image-based tumor phenotyping in a medical system.
Figure 3:
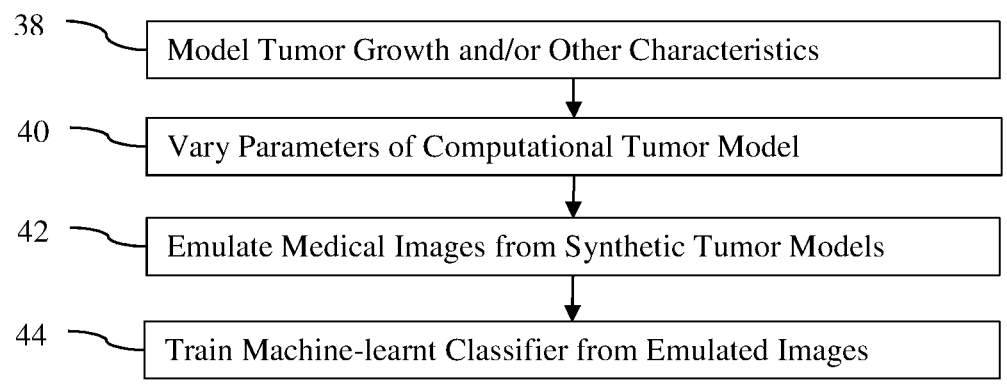
FIG. 3 is a flow chart diagram of one embodiment of a method for machine training for image-based tumor phenotyping in a medical system.

Machine learning has two main phases: a training phase and an application or testing phase. During training, models are learned from labelled clinical data to recognize tumor phenotypes. FIG. 3 shows one embodiment of training. During the testing or application phase, the models are then applied to unseen data for early diagnosis and/or virtual biopsy. FIG. 2 shows one embodiment of application. The training of FIG. 3 is discussed as part of the application of FIG. 2 in order to describe the machine learnt classifier that is trained for the application.

FIG. 2 is a flow chart diagram of one embodiment of a method for image-based tumor phenotyping in a medical system. The method relates to application of a machine-trained classifier for diagnosis, prognosis, therapy planning, delivery, and/or monitoring. The machine-trained classifier is trained for phenotyping cancer tumors. An imaging system model generates synthetic images as training data from tumors created from tumor modeling. Based on a high volume of such training data being available due to modeling, the machine-trained classifier may more accurately phenotype and/or may recognize tumors in more rare situations. The results assist physicians and patients, provide guidance or recommendations, and/or provide a second pathological review.

Figure 4:
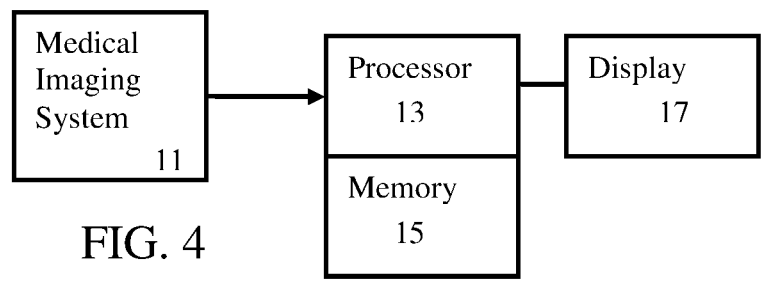
FIG. 4 is a block diagram of one embodiment of a medical system for image-based tumor phenotyping.

The medical system of FIG. 4 or other medical system implements the acts. The system may be a medical imaging system, a hospital workstation, a patient medical records computer, a medical server, a cloud-based system or other secure medical data processing system. The medical system may or may not include a memory or database, such as patient medical record database, oncology data from oncology information system, and/or picture archiving and communications system (PACS).

The acts of FIG. 2 are performed in the order shown (numerical or top to bottom) or other orders. For example, acts 20 and 22 occur simultaneously or in any order. As another example, acts 24 and/or 26 may be performed as part of act 28, such as where a deep-learnt classifier is used.

Additional, different, or fewer acts may be provided. For example, act 30 may not be performed. As another example, act 22 is not performed. Example additional acts include input of features to other machine-learnt classifiers and/or other uses of machine-learnt classification.

In act 20, the medical system acquires medical scan data. The medical scan data is acquired by loading from memory. Alternatively or additionally, the medical scan data is acquired by a medical imaging system, such as an x-ray, computed tomography (CT), magnetic resonance imaging (MRI), molecular imaging (e.g., positron emission tomography (PET), single photon emission computed tomography (SPECT)), ultrasound, camera, or another scanner. The medical imaging system is part of or is the medical system, or the medical system acquires the scan data by transfer from the imaging system over a computer network.

The medical scan data represents a one, two, or three-dimensional region of the patient. For example, in 3-D imaging using any of different modalities, a set of scan data representing intensity at different voxels distributed over three dimensions is acquired. In other embodiments, the medical scan data is two-dimensional representation of a plane or projection through the patient. The medical scan data may be data formatted prior to imaging (e.g., voxels) and/or data formatted as an image for display (e.g., a multi-planar reconstruction or volume rendering).

The medical scan data represents anatomical structures of the patient or patients. Any anatomy may be represented, such as part of an organ with a suspected or known tumor (e.g., CT scan of the heart and surrounding or connected vessels) or, alternatively, whole body images. Medical scan data representing a tumor in tissue of the patient is acquired. Any tissue and any number of tumors may be represented. The tumor may be unknown and/or not easily recognizable as a tumor in an image generated from the medical scan data. The tumor may be of any type and stage.

The medical system may acquire scan data from a past scan of the patient. The different data used for training the model or application for a given patient may either be acquired at the same time or at different times. For example, past medical information and medical images of the patient are used in combination with the current medical information to get a comprehensive picture of the patient condition as well as how the condition has evolved. This information may be sampled in the training database, such as using mathematical models of disease progression (e.g., model of tumor growth), along with the information at a given time, or a combination of these approaches. Several sets of scan data may be used simultaneously in the system, such as scanning with different settings to represent different characteristics of the tumor or patient.

The medical scan data is acquired for a given patient. For diagnosis, prognosis, and/or therapy, the medical scan data for the patient is acquired. The medical scan data is to be used to determine phenotype information about the tumor. One or more medical scans may be used. Phenotype information includes one or more of any characterizing feature of the tumor in the patient. For example, the size, growth rate, border, shape, texture, cellular information, molecular information, stage, type, vascularity, organ of occurrence, patient characteristics associated with the tumor, change in value of any parameter over time, and/or other phenotype information is to be determined, at least in part, from the medical scan data.

In act 22, the medical system obtains other data for the patient. The data is obtained by access to a memory, loading from memory, or transfer through an interface device or network. For example, the data is obtained as part of a web-service to provide the phenotype information. The other data is in one or more memories and/or from one or more sensors. The data is obtained from a computerized medical record, billing database, department records, picture archiving and communications system (PACS), or another source. A textual clinical report for the patient may be mined.

Models may be trained or applied using a multitude of different sources of data. The machine learning algorithms and resulting machine-learnt classifiers use such information as the text in the clinical reports, medical images, medical scan data, blood biomarker information, patient demographics (e.g., age, race, gender, weight, BMI, or others), patient history (e.g., smoking, alcohol consumption, high blood pressure, drug use, current medicines being used, or others), non-invasive measurements (e.g., blood pressure, heart rate, ECG signals, or others), and/or information from other devices and sensors. The models may also use genomic or molecular information from the patient. For example, the presence of specific genomic markers is used to evaluate either the probability of currently experiencing or the predisposition to develop any pathological conditions. Molecular markers like miRNA, mRNA, proteomics, etc. may also be used. The model may use the results of physiological modeling using patient data as input (e.g. blood flow, electrophysiology, biomechanics quantities, or others).

The data is from a past examination of the patient (e.g., previous image, demographics, and patient history) and/or includes current information. For example, a previous examination provides some of the information. Symptoms being currently experienced are also obtained. Other current measurements, such as CT imaging and blood biomarkers, are obtained. Obtaining the same type of data from different times may show progression.

In act 24, the medical system extracts a set of features from the medical scan data and/or the other data. The feature extraction is performed by a medical imaging scanner or on another device, such as an imaging workstation. A processor performs the extraction with or without user input through a user interface. Requests, mining, or searching formatted for the source obtains the data.

The resulting list of values for the features is stored as part of the training database or is used for application of the machine-learnt classifier.

The process of feature extraction from images is fully automated, semi-automated, manual, or a combination of thereof. Under a manual approach, anatomical or other features are input, annotated, or measured by a human operator or user. For example, an imaging scanner or workstation displays a dialog that the user can edit to insert the features. The image is used to determine the values for the features. As another example, the user traces on an image.

Under an automated extraction, the medical system calculates values for the features. Segmentation, thresholding, filtering, template matching, detection (e.g., machine learnt detection), other image processing, or combinations thereof are used to extract values specific to anatomy or the tumor represented in the scan data. Alternatively or additionally, Haar wavelets, steerable features, the intensity values without processing, or other features calculated across the scan data regardless of represented anatomy are used.

Features can also be extracted automatically as part of a deep learning model. In this context, the data is given directly to a deep learning network, which will automatically extract features and perform the machine-learning task in an end-to-end fashion.

Within the medical scan data, the model may use multiple features. For example, tumor size, shape, vascularity, texture, location, and/or other characteristic is determined by image processing. The model may utilize advanced radiogenomic phenotype information inferred from the image. For example, the tumor is detected. The texture of the tumor may indicate the genetic make-up of the patient and/or tumor. Patients with different genes have different types or textures of tumors. Other image indicated phenotype information may be extracted. In other embodiments, the phenotype is extracted from a genetic report or analysis.

A machine-learnt detector or classifier may be used to extract the values for the features. In one implementation, quantitative features are extracted from the image, such as Haar wavelet features. These features are then used to train a machine learning model. Once the model is trained, a similar set of features is also computed for new patients and then fed as input to the model. The model then produces the required outputs as extracted features from the image. One machine-learnt classifier is trained to extract features input to another machine-learnt classifier trained to output tumor phenotype information, providing a cascade of two or more machine-learnt or trained classifiers. The models may use a combination of a wide range of learning algorithms in a cascaded manner. The cascade may be used for imaging and/or the other data. For example, the text in the clinical reports is processed using machine-learnt natural language processing tools to identify the key information content.

As another example, medical scan data and/or other data are processed by any machine learning models including deep convolutional neural networks, kernel based methods, or others. For example, a deep learning network is automatically extracts the most relevant features and performs the learning task together. The information and features extracted from these different sources is then aggregated to train a complex higher-order model or machine-learnt classifier, which predicts the diagnosis, prognosis, and/or treatment outcome. Where a deep learnt classifier is used, the initial layers of the neural network learn to extract features in act 24. In application, the medical scan data and/or other data is input to the machine-trained classifier as the features. The initial layers extract further features in act 24 and input those extracted features in act 26 into subsequent layers of the neural network for the determination of act 28, so the extraction and input are part of the determination 28. In this context, the scan data and/or other data is the features that are extracted and input.

In acts 26 and 28, the medical system applies one or more machine-learnt classifiers. The input of the extracted features from act 24 in act 26 results in the output or determination for act 28. A processor inputs the features, applying the machine-learnt classifier to the input features to determine the diagnosis, prognosis, treatment outcome, and/or other phenotype information. In one embodiment, the determination is of tumor characteristics. This output is used to derive diagnosis, prognosis, and/or treatment outcome (e.g., treatment recommendation) based on known relationship to the tumor characteristics. In other embodiments, the determination is of the diagnosis, prognosis, and/or treatment outcome as the output of the classifier.

The output may be a diagnosis, such as a type, stage, benign or malignant, or another characteristic of the tumor. The output may be prognosis, such as a time to reach a next stage, a life expectancy, a time to spreading, a predicted size, reoccurrence, or another prediction. The output may be a treatment outcome, such as likely effectiveness of one or more treatments, cost of treatments, side effect of treatments, and/or other treatment-related guidance.

For training, the extracted features and known ground truth (i.e., tumor phenotype information, diagnosis, treatment outcome, and/or prognosis) for the samples of the training data are used to learn to classify. The input feature vectors and corresponding results for many samples are used in machine learning. Tens, hundreds, or thousands of examples are used to train. Greater numbers of training examples may result in more reliable classification. The corresponding feature values are used to map the feature values to the results.

One classifier predicts one result. One classifier may be trained to predict multiple types of results. For example, the same classifier predicts two or more of the diagnosis, prognosis, and/or treatment outcome. The classifier may predict the diagnosis and then look-up is used to determine prognosis. Alternatively, different classifiers are used for different types of results, such as one classifier indicating a diagnosis and another classifier in a cascade indicating the prognosis and/or treatment outcome.

Rather than training one classifier, the classifier may be learned as a network of different models, where each model works on some subset or the entirety of the feature space. The outputs from each model may be used as inputs to other models, thereby creating new features. The output from one model may be used as an input to the same model to produce recursive model estimates. The classifier may be trained to learn from categorical, discrete, and/or continuous features. The classifier may be a combination of multiple interacting machine-learnt classifiers, each of which use the same or a different subset of features. The outputs from one model can be used as an input to another classifier.

In one embodiment, the machine-learnt model is implemented as a neural network. Such networks have a pool of shared layers to determine common features to the task at hand and additional layers that are trained for classification from the features. Any type of machine learning algorithm may be used, such as a support vector machine. The machine learning is supervised, semi-supervised, or unsupervised. Some examples using supervised learning include regression, instance-based methods, regularization methods, decision tree learning, Bayesian, kernel methods, clustering methods, association rule learning, artificial neural networks, dimensionality reduction, and ensemble methods. Probabilistic boosting tree, hierarchal, or other processes may be used.

The machine learning may use all of the input features. Alternatively, the machine learning determines discriminative features and selects a feature set to be used for classifying. A subset of the extracted features may be used for learning, as determined from feature selection and ranking, feature combination, or other process.

Collecting a statistically significant number of training samples (e.g., thousands of patients with known results for a given condition or number of conditions) may be difficult. Many samples are desired for each unique arrangement (e.g., tumor characteristics specific to the tumor and/or including patient characteristics relevant to the tumor). Acquiring the samples from actual patients may be difficult, especially with known outcomes to use as ground truth in training. Some of the training data may be synthetically generated to fill any gaps, or the entirety of the training data is synthetically generated. It may be difficult to locate many samples of patients suffering from one or more conditions, combination of conditions, or specifics to a condition (e.g., two tumors, rare cancers, unusual growth patterns, males with breast cancer, tumor in atypically stiff or soft tissue, tumor of a type not common with a particular gene of the patient, etc.). Synthetic examples may be created. Rather than using specific existing patient cases for the training data, data not specific to an existing or previously handled patient is used. The synthetic sample is generated in-silico with a known outcome. An actual patient may be the starting point, but the modeling creates a tumor representation not specific to a given patient. A value of one or more parameters of the tumor model are changed to create a different sample than provided by the actual patient. The machine-trained classifier is trained only from synthetic data or from a combination of data from a collection of patients and synthetic data.

The synthetic data may be for the other data and/or the medical scan data. In one embodiment, the synthetic data is of medical images or other medical scan data. The machine-trained classifier is trained from examples of scan data generated with computer modeling, physical modeling, or both computer and physical modeling using in vitro or in silico models and corresponding ground truths. A tumor model is provided with different values of one or more parameters, resulting in different synthetic tumors. An image simulator then simulates generation of one or more sets of scan data from each of the tumor models. The resulting synthetic scan data samples are stored in a database. The values of the parameters, the synthetic tumors, and/or information derived therefrom (e.g., pathological condition being modeled) are stored in the database as the ground truth for the synthetic images.

FIG. 3 is a flow chart diagram of one embodiment of a method for machine training for image-based tumor phenotyping in a medical system using a database populated, at least in part, by synthetically generated scan data. The approach of using synthetic images and datasets has the advantage of being able to span pathological conditions that are relatively rare and hard to sample from the patient population in sufficient numbers. The large number of variations available is one benefit of using synthetic data for training. Actual examples from patients may also be used to populate the database or no actual examples are used.

The acts are performed in the order shown or a different order. Additional, different, or fewer acts may be used, such as combining acts 38 and 40.

The method is implemented by a server (local or cloud-based), computer, or workstation as the medical system using tumor models. Any medical system for training a machine to determine phenotype information for tumors may be used. The same or different medical system used for implementing the method of FIG. 2 is used for implementing the method of FIG. 3.

In act 38, the medical system models tumors. Any mechanistic or computational tumor modeling may be used. Rather than using tumors from an actual patient, a model of the tumor is used. Studies or other research may provide the computational model. The computational model is defined by parameters that control characteristics of the synthetic tumor. Different tumors may be created by different values of the parameters.

In one embodiment, the computational model is of tumor physiology (e.g., growth and/or shrinkage). The model provides for tumor characteristics (e.g., size, shape, vascularity, etc.) by representing growth or shrinkage of the tumor from an initial geometry (seed, sphere, etc.). The computational model may be for other characteristics than growth.

Mathematical modeling of cancer has been an extensive research area as a tool for disease understanding, hypothesis testing, drug design, and pre-clinical trial testing. Various models have been proposed, spanning from pharmacokinetic models of the molecular interactions involved in tumors to three-dimensional (3D), phenomenological tissue-level approaches. Any of these or other models may be used.

In one embodiment, 3D computational models of tumors augment the database used for training radiomics or radiogenomics predictive models (i.e., machine-learnt classifier). The tumor model is generative, so any type of tumors, at any time of the tumor development process, and/or for any "host" tissue or organ, accordingly, may be used to generate a synthetic 3D lesion with known properties.

In one embodiment, the mathematical modeling of cancer uses a multi-scale model of tumor physiology. Multi-scale models include information at two or more of the molecular, cellular, tissue, and/or other scales. Other models than multi-scale may be used. At the tissue scale, tumor growth is modeled as a reaction-diffusion process, where the reaction is linked to the cellular aspects of the tumor growth and activity and the diffusion is linked to the cellular motility. Both reaction and diffusion terms may be modeled at a macro-scale using traditional laws (e.g. Gompertz or exponential tumor growth model). More detailed models may be used to generate additional or a greater number of plausible, synthetic cancer configurations for training. For example, angiogenesis and tumor vascularization is coupled to the growth model to take into account the metabolic part of the tumor. This enables simulation of cellular necrosis and quiescence (e.g., due to lack of oxygen) and angiogenesis (e.g., macroscopic or 3D, fractal-like model). The growth model is also coupled with the extra-cellular matrix (e.g., space in between cells) to take into account the interstitial pressure variation due to the tumor, which triggers angiogenesis and tumor infiltration. The interstitial pressure gradient also modulates the nutrients flow, and therefore tumor cell function (e.g., duplication, death, quiescence) and shape. Tumor growth is also coupled with the neighboring tissue using biomechanical models to mimic the displacement of healthy tissues due to the tumor mass. The biomechanical model may account for tissue stiffness or other characteristics effecting the interaction with the modeled tumor.

Additional, different, or fewer mechanisms may be replicated by the tumor models. Any complexity for modeling the tumor may be used. Models that include genetic data, gene expression, miRNA and mRNA pathways analysis, or other type of molecular, cellular or clinical data may be used.

The mechanistic or computational tumor model is represented by one or more equations. The equations for the mechanisms may include any spatial representation, such as solving in 3D using the finite element method as a series of partial differentiations. To handle a large number of simulations, the Lattice Boltzmann method may be used to solve the reaction-diffusion-advection equations related to the model using point or mesh node computations. Biological phenomena that happen in a very short time frame compared to the observation scale may then be modeled as traveling waves and solved very efficiently using graph-based algorithms (e.g. shortest-path). The border of the tumor is treated as a traveling wave.

In additional or different embodiments, the mechanistic or computational model is or includes a machine-learnt classifier. The tumor growth model is learnt using artificial intelligence approaches, such as multi-agent systems and deep reinforcement learning. Each cell is an agent that evolves in the 3D extra-cellular matrix and communicates or interacts with other agents. The laws governing the agent are explicitly modeled, which may require high computation time. The agent-based system is another solver. The agent laws may be machine learnt using deep learning approaches to reduce computation time. The cellular physiology equations are approximated by a neural network that, given the state of the agent and of its environment (e.g. level of oxygen and other nutrients, hormones, molecular markers, interstitial pressure, etc.), returns the next plausible cellular action (e.g. duplication, death, quiescence, etc.). Deep reinforcement learning techniques could be used to train the agents to directly achieve the end-point simulated by macroscopic models.

The machine-learnt classifier is trained from data from actual patients and/or from measurements of actual tumors or tumor cells, such as in a wet lab. Alternatively, the explicit agent models are used to create synthetic examples used for training the computational tumor model. The agents learn by interacting with the environment (a model of the extracellular matrix), and get a reward of 0 until the current global state is equal to the target state, where the reward would be 1. With such a framework, the target state not only comes from simulation (macroscopic models), but also from in-vitro, 3D model of tumor growth, where high-resolution molecular imaging may be performed.

While actual examples may be used, the resulting tumor model is able to create other synthetic examples using the knowledge gained through machine learning. Where the computational or mechanistic tumor model uses the machine-learnt classifier for only one aspect (e.g., cellular state), equations or other computational modeling are also used to create the synthetic data. In other embodiments, machine learning is used to create the computational model as the entire tumor model.

In act 40, the medical system (e.g., processor) varies parameters of the computational tumor model. The tumor model is defined by one or more parameters, such as any of the modeling parameters in the equations or used as input features in the computational model. The interaction of the modeled tumor with healthy tissue may be parameterized, so the values of the parameters for this interaction may be varied.

A starting model may be created from a given patient, but the majority of training examples are based on alterations from the starting model. Alternatively, the starting model or models are averages or other models not directly related to a given patient. The data is synthetic by not being extracted from data for particular patients to represent that specific patient (i.e., the model is not specific to a patient). The digital representation is generated and stored on a computer. In alternative embodiments, some or a majority of the training examples are extracted from patient-specific data for a plurality of patients and only some of the examples are alterations of those models or created without actual examples as starting points. If real patient anatomies are available, further synthetic models may be constructed by stochastically perturbing the features of the patient or tumor anatomy and/or the values of variables in the computational model. This added synthetic data may be used to get a richer representation, which may account for uncertainties in the data.

To model any given condition, the values of the parameters are set. Other values may be provided for other parameters to produce further examples for a given condition. Other values of some parameters may be used to model different conditions. By varying the values, a set of tumor models are generated synthetically. Additional examples for training are created by altering one or more values of variables for the tumor. Any number of different parameters may be varied. Hundreds or thousands of different examples for training may be generated from a single starting model.

The variation may be controlled or user set. Alternatively or additionally, the variation is random. For example, thousands of stochastic perturbations to the synthetic tumor model produce thousands of corresponding tumor models. Since the tumor models have known conditions (e.g., known phenotype information to be used as the ground truth), a rich dataset on which to train the machine learning model is provided. The stochastic variation may be of parameters with a same condition or type of tumor. Alternatively, the stochastic variation samples across conditions or types of tumors.

To populate the database, different approaches may be used. One or more baseline models, whose properties are then randomly or systematically perturbed to obtain a large number of models, are created. In another approach, each model is generated separately by following a set of rules and by randomly or systematically perturbing the parameter values of these rules. Scaling laws may be used for generating realistic synthetic models.

The values of the parameters are either chosen randomly for each synthetic example (e.g., true or false for binary variables or a value in a predefined range for continuous variables) or the entire parameter space is explored systematically within limited ranges when generating the database of synthetic examples. Any type of distribution may be used for the continuous variables, such as uniform, normal, or other. Known, estimated, or standard normal distributions may be used. Other sources of variability may be used to create the synthetic examples for training.

A library of tumor models is created. The end result of the tumor model is a virtual, 3D "host" organ affected by a virtual 3D tumor. The 3D tumor may include heterogeneous tissue and cellular characteristics. Different cell types may lead to different cancer morphology and physiology, which may be captured with different mathematical laws or learned agents. Different libraries for different collections of tumor models, such as by type of tumor, may be created. Alternatively, a single library is created, such as for a desired type or types of tumors. The library of tumor models may be automatically or interactively selected during the generation of the synthetic data. The library contains different models for a given tumor type, with potentially different laws according to the stage of cancer to mimic. Different tumor models according to the seed cell type may alternatively or additionally be included.

In one embodiment, the library is created based on a template image or scan data (e.g., 3D mesh or voxel representation) of healthy tissue or tissue with a tumor. Given the template scan data, automatic image parsing is performed to extract the main organ and/or tissues of interest. The user or processor picks a seed location within an organ or tissue for the tumor. The system would then recognize which organ has been selected, and the most likely tumor (e.g., based on population analysis) is automatically selected and virtually simulated at that location with various perturbations. Alternatively, a list of plausible cancers that may be generated at that location (e.g., determined according to the cellular characteristics) is given to the user or processor. One or more plausible cancers are selected and modeled in the template. Another option is to give total freedom to the user or processor to implant any tumor seed cell at the selected location, such as to mimic a metastasis. In other embodiments, the location is varied by the user or processor to create the tumor models.

The tumor modeling may be used once the tumor phenotype for a patient is identified. The template image given to the virtual cancer system is from the patient. The system automatically recognizes the location of the tumor. The virtual tumor is selected based on the output phenotype information. The tumor is simulated. Because the underlying image is pathological, the system may then compare the appearance of the simulated virtual tumor with the real-image to automatically tune the parameters of the tumor model and further refine the realism of the virtual tumor, resulting in a more realistic, synthetic tumor model. This tumor model may be used for this patient, such as to explore the effects of treatment for that patient. In other embodiments, this refined tumor model or perturbed variations may be included in the library for training.

One parameter of the modeling that may be varied is time. The tumor is modeled at different stages or period of development. This variation is used to create samples for training. Where the input feature vector uses scan data from different times for progression analysis, then the samples from different times may be used to show variation in progression.

The resulting virtual pathological anatomy from the tumor modeling is then used as basis for the synthetic image generation. Each of the synthetic tumors with or without scan data representing healthy tissue is used to generate an image or images. "Image" represents scan data prior to reformatting for display, such as 3D voxel representation, or scan data as formatted for display on a 2D display device. The use of image accounts for effects of the imaging modality.

In act 42, the medical system emulates medical images from the synthetically generated tumor models of the set. The various tumor models are used to generate one or more images. Synthetic images are created with an image model from the modeling of tumor growth. The images emulate scanning the tumors and healthy tissue by a medical imaging system or scanner. By modeling the image forming process or the medical scanner, a synthetic image is generated from the synthetic tumor model. For example, the image formation process of a CT scanner is applied to the anatomical model, resulting in a synthetic image simulating medical scanning of the synthetic and/or actual anatomy. Any forward modeling or image formation model may produce the synthetic image.

The image reconstruction is performed using a system matrix or system operators providing interaction (e.g., sensitivity) between the virtual medical scanner and the synthetic tumor. In one embodiment, the synthetic tumors are converted to synthetic medical images by generating or using parametric maps relevant to the imaging modality being synthesized, and then simulating a scan by the imaging modality using the parametric map. In general, the parametric maps are a set of quantitative images of all the tissue properties having an influence on the resulting image at each voxel. The exact nature of the maps depends on the modality. Once the parametric maps are synthesized, any virtual scan of the tumor may be synthesized by changing the configuration of the scanner.

The parameters in the parametric map may be different for different modalities. Any modality may be used, such as x-ray, CT, MRI, PET, SPECT, or ultrasound (e.g., contrast-enhanced ultrasound). X-ray modalities, including CT, measure x-ray attenuation and reconstruct X-ray absorption coefficient images. The absorption coefficient may be computed from the chemical composition of the tissue and known mass absorption coefficients for the present isotopes. By calibrating for typical compositions or compositions indicated in the tumor model, images may be generated from the computational tumor models. The calibration for composition may be performed at the tissue and/or cellular scale. From the cellular, macroscopic tissue fractions are modeled from the cell and interstitial sizes.

Basic MR imaging is sensitive to the longitudinal and transverse tissue proton relaxation constants T1 and T2, with water and lipid molecules being the dominating sources of protons observed. At coarser scales than the atomic level, spin relaxation depends on the temperature, molecular binding of the proton, and chemical exchange possibilities. Any MR model may be used, such as models for dynamic contrast-enhanced MRI. The generative exchange rates may be estimated from the MRI images and used to model MR imaging. Isotropic diffusion may be modeled in a similar way. T1 and T2 are generated from multi-compartment tissue models with calibrated base values for individual components (cell types, interstitial space, vessels, etc.) and exchange rate between them, and volume fractions obtained from the computational tissue model.

Additional samples for training are created by altering the emulated images or the image model simulating image formation. For example, the processor adds different degrees of statistical noise to each of the emulated medical images, resulting in a plurality of additional images for each of the emulated medical images. Other parameters than noise may be altered, such as altering imaging settings (e.g., dynamic range, gain, source intensity, detector sensitivity, focus, and/or others). The result is additional synthetic images with known ground truth for training.

To increase robustness, different transformations may be applied to the training data to produce additional training samples. For instance, different degrees of statistical noise are applied to medical images (synthetic or actual) to produce additional synthetic medical images. The addition of the noise does not alter the ground truth, allowing for the machine training to learn to provide the same final prediction regardless of the noise level. Noise may be introduced into the tumor model. Other variations in the image and/or model may be used, such as translation, scale, and/or rotation to produce additional images from a given sample.

In one embodiment, the parameters of the tumor and/or image models are adjusted by combining data from microscopic imaging and chemical testing where medical images of tumors with known phenotype are available. Maximum likelihood training is used based on the microscopic imaging, chemical testing, and/or imaging. Tumor and image models feature hiding parameters that may not be measured directly. Maximum likelihood training refines the models to help explain the available observables, such as images, chemical tests, and/or pathology slices. Once the parametric maps are generated, scan simulation tools generate the images or other scan data.

The library, created at least in part or completely from simulated images based on synthetic tumor samples, is used for training. In act 44, a machine trains the machine-learnt classifier using, at least in part, the simulated medical images. A processor performs the machine learning using the training data.

Using synthetic modeling instead of requiring examples from a large collection of patients for training data provides several advantages. A very large number of cases may be automatically generated, leading to an extensive database. Complex pathological configurations may be generated, such multiple tumors, tumors in atypical locations, atypical tumors, tumors in atypical patients, or other situations. Rare pathological cases may be sampled better. Since the generation of synthetic, in-silico tumors may be completely automated, the cost of generating a large database is reduced as compared to assembling patient examples. The examples may be extended to different demographic groups easily. The training may be done in a global manner or a site-specific manner, allowing the system to account for tumor trends based on patient demographics and epidemiology. Finding sufficient examples in a local region may be difficult, but is not a difficulty when using synthetically generated tumors and scan data. The training may be iteratively improved with either more data or with better representations of the features.

Once the synthetic images (e.g., scan data) have been generated, the features which are used for training the machine learning algorithm are extracted from the images. The same features or some subset of the features are extracted from the medical images of the patient in application and used for predicting the results using the trained model. Depending on the source and type of the input data, the extracted features may be binary, numerical, categorical, ordinal, binomial, interval, text-based, or combinations thereof. Features from scan data and/or features from other data (see act 22) may be used for training.

Any type of features may be used. Morphological features may be used. The machine learning process may provide for certain features to be used and others not to be used. To train, the features to be used may be selected by a programmer. Some example features may include the parameters used or selected to define or create the anatomical model. Other or different features may additionally or alternatively be extracted. For deep learning, the input is the data and the learning creates filter kernels or other definitions of features from the data.

The simulated medical images and/or other data are used to train, by a machine, the machine-learnt classifier. Any type of machine learning may be used. In one embodiment, a deep-learnt classifier is trained, such as using a neural network. The machine-learnt classifier is trained to predict from the database of training data including the images created from the modeling of the tumor, such as modeling tumor growth. The known outcomes or ground truth phenotype information is used to statistically relate the input features to a prediction of the phenotype information. A matrix or matrices representing the machine-learnt classifier are created from the training data and ground truth.

The machine-learnt classifier is trained to output phenotype information, such as diagnosis, prognosis, and/or treatment outcome for the tumor associated with input data. For example, the machine-learnt classifier is trained to predict a tumor grade, tumor stage, therapy response, benign or malignant, tumor cell differentiation, or prognosis. The machine-learnt classifier is a radiomics model. Where genetic information is included, the machine-learnt classifier is a radiogenomics model.

After the synthetic, realistic images are generated, different types of radiomics models may be trained. The radiomic model may be a single-time point prediction model. The prediction task may include, but is not limited to, tumor grade prediction, tumor staging, therapy response prediction, tumor benign/malignant classification, tumor cell differentiation, prognosis indication, treatment planning, or other classification of phenotype based on scan data from one point in time. Other data may be from that point in time or other points in time. An image patch covering the tumor and surrounding tissue is extracted from the synthetic medical image for training. During the training phase, the set of patches extracted from all the synthetic medical images is fed into a machine learning algorithm that learns the optimal feature presentation for predicting the output. The machine learning algorithm learns a representation, or a radiomics model, that may be later applied to an image patch or patches from a real medical image or scan data.

The radiomic model may be a multi-point prediction model. The machine-learnt classifier is trained to classify from patient images over time. Based on the tumor growth model, tumor images corresponding to the same tumor at different time points may be generated. The aforementioned single-time point prediction tasks apply to multi-time point as well. During the training phase, the image patches extracted from different time points are presented as different input channels to the machine learning algorithm.

In addition to assisting for individual patients, the machine-learnt classifier may be used to create plans or guidelines. Unlike typical CT or PET scans, there is no concern of radiation dose during for the synthetic image acquisition. The cost to create by modeling is less than creation by actual scanning (e.g., MRI is expensive). Without these limitations, a greater number of time points may be included. A very large number (e.g., tens or hundreds) of time points may be used. Such a range of time points may allow for determining a tradeoff between cost, radiation dose, and prediction accuracy. The machine learning is trained based on cost, dose, and/or accuracy outcomes for many time points. Healthcare administration and policies may be established based on study. The answer (e.g., guidelines for optimal cost, dose, and/or accuracy) may be country specific and/or hospital specific. Using the training, an optimal diagnosis, decision support, and/or treatment plan may be provided for each hospital.

From a clinical point of view, the optimal time points for imaging of an actual patient may be determined. The optimal combination of different image modalities may be determined. The optimal staging criteria for different types of cancers may be determined. The relationship between tumor image appearance with other clinical data (patient demographics, age, sex, etc.) may be determined.

Where the machine-trained classifier is a neural network or other layered classifier, information from processing within the machine-learnt classifier may be output. For example, extracted feature values are output from a deep-learnt classifier. These extracted features from one or more layers of the classifier may be visualized to provide information. To aid the understanding of the interplay of different time points, different layers of the multi-layer (deep) neural network may be visualized. This is akin to visualizing a manifold and may not be possible with only a limited number of time points to sample. Using virtual experiments, a continuous manifold may be generated.

In other embodiments, the machine training provides for multi-tumor interaction at a single-time point. In patients with multiple tumors (e.g., consisting of primary and/or metastases), the radiomics model may learn treatment options for specifically targeted tumors. In yet other embodiments, a multi-tumor, multi-time point radiomics model is learnt.

Returning to the application of the machine-learnt classifier of FIG. 2, the medical system determines the result in act 28. The extracted features for a particular patient are input in act 26. The results are any of the phenotype information or information derived from phenotype information, such as diagnosis, prognosis, and/or treatment outcome (e.g., therapy response). The trained machine is applied to an image of a patient to predict a tumor characteristic of a tumor represented in the image of the patient. For a given patient, the machine-learnt classifier determines the results from the input feature vector. The machine-learnt classifier determines the result or determines information that may be used to derive the result, such as based on a clinical study or expert knowledge showing the relationship.

Once trained, the machine-learnt classifier is instantiated as a matrix or matrices. The matrix maps the values of the input features to values of the result (e.g., phenotype information). This mapping is used to predict the result in 28. For example, a type of tumor, stage of tumor, prognosis, life expectancy, an outcome for treatment of the patient, or combinations thereof are predicted by the processor applying the values of the features to the machine-trained classifier. The prediction or result may include probabilistic information, such as a probability or confidence score for the result or over a range of different possible results (e.g., 70% stage three, 25% stage two, and 5% stage four).

The machine-learnt model is hosted as a local application, for instance running directly on a medical scanner or a workstation connected to the patient information systems. Alternatively, the machine-learnt model is hosted as a service on a networked machine, such as a public or private cloud deployment with a server hosting the machine-learnt model.

In act 30, the phenotype information and/or information derived therefrom is output. The output is to a memory, network, computerized patient medical record, and/or a display device. The output from the model may be a clinical report with key findings presented in a structured format for easy search and retrieval. Other outputs may be used, such as an alert, notification, filling in one or more fields in a patient medical record, or to a display. Any image of the tumor may be provided with annotations from the results. Values of parameters of a computational model best matching the tumor of the patient may be output.

FIG. 4 shows a medical system for training and/or application of a machine-learnt classifier for tumor information. The medical system includes a medical imaging system 11, a processor 13, a memory 15, and a display 16. The processor 13 and the memory 15 are shown separate from the medical imaging system 11, such associated with being a computer or workstation apart from the medical imaging system 11. In other embodiments, the processor 13 and/or memory 15 are part of the medical imaging system 11. In alternative embodiments, the medical system is a workstation, computer, or server. For example, the medical imaging system 11 is not provided or is provided for acquiring data representing a volume, and a separate database, server, workstation, and/or computer is provided for extracting features and applying a classifier to predict one or more results. Additional, different, or fewer components may be used.

The system is used for application of a machine-learnt model (e.g., one or more machine-learnt classifiers). In alternative embodiments, the system is used for training with machine learning and/or generation of the examples in the database. Where only synthetic samples generated from a computational model of a tumor is used, the medical imaging system 11 may not be provided. Where the samples of the library, even if from actual patients (e.g., scan data representing actual scans), are stored in the memory 15, the medical imaging system 11 may not be provided.

The computing components, devices, or machines of the medical system, such as the medical imaging system 11 and/or the processor 13 are configured by hardware, software, and/or firmware to perform calculations or other acts. The computing components operate independently or in conjunction with each other to perform any given act, such as the acts of any of the methods described above. The act is performed by one of the computer components, another of the computing components, or a combination of the computing components. Other components may be used or controlled by the computing components to scan or perform other functions.

The medical imaging system 11 is any now known or later developed modality for scanning a patient. The medical imaging system 11 scans the patient. For example, a C-arm x-ray system (e.g., DynaCT from Siemens), CT like system, or CT system is used. Other modalities include MR, x-ray, angiography, fluoroscopy, PET, SPECT, or ultrasound. The medical imaging system 11 is configured to acquire the medical imaging data representing the patient. The scan data is acquired by scanning the patient using transmission by the scanner and/or by receiving signals from the patient.

The memory 15 is a buffer, cache, RAM, removable media, hard drive, magnetic, optical, database, or other now known or later developed memory. The memory 15 is a single device or group of two or more devices. The memory 15 is within the system 11, part of a computer with the processor 13, or is outside or remote from other components.

The memory 15 is configured to store medical scan data, other data, extracted features, examples (e.g., training data or data from other patients), and/or other information. Output results, information derived from the results, or calculations used to determine the results are stored in the memory 15. The memory 15 stores one or more matrices for the machine-learnt classifier or classifiers.

The memory 15 is additionally or alternatively a non-transitory computer readable storage medium with processing instructions. The memory 15 stores data representing instructions executable by the programmed processor 13. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 13 is a general processor, digital signal processor, three-dimensional data processor, graphics processing unit, application specific integrated circuit, field programmable gate array, digital circuit, analog circuit, combinations thereof, or other now known or later developed device for processing data. The processor 13 is a single device, a plurality of devices, or a network. For more than one device, parallel or sequential division of processing may be used. Different devices making up the processor 13 may perform different functions, such as extracting values for features by one device and applying a machine-learnt classifier by another device. In one embodiment, the processor 13 is a control processor or other processor of the medical imaging system 11. The processor 13 operates pursuant to stored instructions to perform various acts described herein.

The processor 13 is configured to extract values for features, to input the values, to output results, and/or to derive information from output results. The processor 13 applies the machine-learnt model to data for one or more patients. The diagnosis, prognosis, therapy response, and/or other information is determined by the processor 13 for a tumor or tumors of a patient.

The display 16 is a CRT, LCD, plasma, projector, printer, or other output device for showing an image. The display 16 displays the results or information derived from the results.

Probabilities associated with any prediction, supporting data (e.g., values of input features), images from the medical scan data, and/or other information are output to assist the physician.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for image-based tumor phenotyping in a medical system, the method comprising:
    acquiring medical scan data representing a tumor in tissue of a patient;
    extracting a set of features from the medical scan data;
    inputting the features to a machine-trained classifier, the machine trained classifier trained, at least in part, from training data comprising images generated synthetically from tumor models to not be specific to existing patient cases and having different tumor pathologies than in a database of the training data, the images generated synthetically based on a tumor model;
    determining, by the medical system using application of the machine-trained classifier to the features, phenotype information of the tumor; and
    outputting the phenotype information characterizing the tumor in the tissue of the patient.

2. The method of claim 1 wherein acquiring comprises acquiring computed tomography data, magnetic resonance data, or molecular imaging data.

3. The method of claim 1 further comprising obtaining other data for the patient, the other data comprising symptom, patient demographics, blood biomarkers, patient history, non-invasive measurements, extracts from a clinical report, genetics, or combinations thereof, wherein inputting comprises inputting the other data, and wherein determining comprises determining by application of the machine-trained classifier to the features and other data.

4. The method of claim 1 wherein the machine-trained classifier comprises a deep learnt classifier, and wherein extracting comprises extracting the set of features as part of the determining where the application inputs the features to a subsequent layer of the machine-trained classifier.

5. The method of claim 1 wherein determining comprises determining with the application of the machine-trained classifier where the machine-trained classifier is trained, at least in part, from the synthetically generated images, where the synthetically generated images are a combination of a model of one or more scan modality with the tumor model.

6. The method of claim 1 wherein determining comprises determining with the application of the machine-trained classifier where the machine-trained classifier is trained, at least in part, from the synthetically generated images, where the synthetically generated images are generated using a multi-scale model of tumor physiology as the tumor model, the multi-scale model including molecular, cellular and tissue scales.

7. The method of claim 1 wherein determining comprises determining with the application of the machine-trained classifier where the machine-trained classifier is trained, at least in part, from the synthetically generated images, where the synthetically generated images are generated from perturbation of the tumor model.

8. The method of claim 1 wherein determining comprises determining with the application of the machine-trained classifier where the machine-trained classifier is trained, at least in part, from the synthetically generated images, where the synthetically generated images are generated from a machine-learnt model of cellular physiology of the tumor model.

9. The method of claim 1 wherein determining comprises determining with the application of the machine-trained classifier where the machine-trained classifier is trained, at least in part, from the synthetically generated images, where the synthetically generated images are generated with at least one model of a scanning modality.

10. The method of claim 1 wherein determining the phenotype information comprises determining a diagnosis of the tumor and/or a therapy response.

11. A method for machine training for image-based tumor phenotyping in a medical system, the method comprising:
    varying parameters via interactively or automatically of a computational tumor model, the varying providing a set of synthetically generated examples of tumors including examples not specific to any actual patients and having different virtual pathologies than in any training database;
    emulating, by simulation of imaging, medical images from the synthetically generated examples of tumors; and
    training, with a machine of the medical system, a machine-learnt classifier using the emulated medical images as training data with samples including the different virtual pathologies.

12. The method of claim 11 wherein varying comprises varying the parameters with the computational tumor model comprising a multi-scale model, a machine-learnt model, or both.

13. The method of claim 12 wherein the machine-learnt model comprises a machine learnt model of cellular state.

14. The method of claim 11 wherein varying comprises varying with the computational tumor model including interaction of the tumors with healthy tissue, and wherein emulating comprises emulating from the examples of the tumors and healthy tissue.

15. The method of claim 11 wherein emulating comprises generating parametric maps of characteristics that interact with an imaging modality from the examples of the tumors, and simulating a scan by the imaging modality using the parametric map.

16. The method of claim 11 wherein training comprises training the machine-learnt classifier to predict a tumor grade, tumor stage, therapy response, benign or malignant, tumor cell differentiation, or prognosis.

17. The method of claim 11 wherein training comprise training a deep-learnt classifier as the machine-learnt classifier.

18. The method of claim 11 wherein varying comprises varying an amount of time, and wherein training comprises training the machine-learnt classifier to classify from patient images over time.

19. A method for machine training for image-based tumor phenotyping in a medical system, the method comprising:
    modeling tumor physiology via interactively or automatically changes, the modeling providing samples of various tumor anatomies different than in a training database;
    creating synthetic images with an image model from the various tumor anatomies from the modeling of tumor physiology; and training a machine by the machine training to predict from just the database of training data including the images created from the various tumor anatomies from the modeling of the tumor physiology.

20. The method of claim 19 further comprising applying the trained machine to an image of a patient to predict a tumor characteristic of a tumor represented in the image of the patient.

* * * * *